United States Patent [19]

Bobrow et al.

[11] Patent Number: 5,238,817
[45] Date of Patent: Aug. 24, 1993

[54] CHROMOGENIC SUBSTRATES FOR IMPROVING DETECTION IN A PEROXIDASE-BASED ASSAY

[75] Inventors: Mark N. Bobrow, Woburn; Gerald J. Litt, Wellesley, both of Mass.

[73] Assignee: E. I. Du Pont de Nemours and Company, Wilmington, Del.

[21] Appl. No.: 729,378

[22] Filed: Jul. 12, 1991

[51] Int. Cl.$^5$ .................. C12Q 1/28; C12N 9/96
[52] U.S. Cl. .................. 435/28; 435/7.92; 435/25; 435/188; 436/815; 436/904
[58] Field of Search .......... 435/28, 25, 7.92, 188; 436/904, 815

[56] References Cited

U.S. PATENT DOCUMENTS

| | | | |
|---|---|---|---|
| 4,503,143 | 3/1985 | Gerber et al. | 435/7 |
| 4,596,770 | 6/1986 | Parham et al. | 435/28 |
| 4,615,972 | 10/1986 | Gallacher | 435/28 |
| 4,777,143 | 10/1988 | Price et al. | 436/129 |
| 4,849,342 | 7/1989 | Ben-Michael | 435/7 |
| 4,886,760 | 12/1989 | Ben-Michael | 436/66 |
| 5,116,733 | 5/1992 | Yamasaki | 435/28 |

FOREIGN PATENT DOCUMENTS

| | | |
|---|---|---|
| 0271713 | 6/1988 | European Pat. Off. |
| 62-8055 | 1/1987 | Japan |

OTHER PUBLICATIONS

Conyers et al, *Anal. Biochem.*, vol. 192, pp. 207–211 (1991).
Bos et al, *J. of Immunoassay*, vol. 2, Nos. 3 and 4, pp. 187–204, 1981.
Brand et al., BioTechniques, 8(1): 58–60 (1990), describes a comparison of the performance and stability of two precipitating substrate systems for immunoblotting, namely, TMB and DAB.
Kobayashi and Tashima, "Visualization of Antigen on Nitrocellulose Membrane by the Oxidative Coupling Reaction of N,N'-Dimethyl-p-phenylenediamine and 4-chloro-1-naphthol," Analytical Biochemistry 183, 9–12 (1989).
Kirkegaard & Perry Laboratories, Inc. 1993 Catalog, "Substrates for Use with Peroxidase-Labeled Antibodies," pp. 47–52.
De Jong et al., Histochemical Journal 17:1119–1130 (1985) describes various visualization methods for peroxidase and alkaline phosphatase activity with respect to sensitivity, stability of chromogen solutions and final precipitates, background staining, and localization properties.
Nachlas et al., J. Histochem. Cytochem., 6: 445–456 (1958), describes 4-amino-1-N,N-dimethylnaphthylamine useful as a reagent for the Nadi reaction which can provide a histochemical method for either cyctochrome oxidase (G-Nadi) or peroxidase (M-Nadi).
Kirkegaard & Perry Labs, Product Catalog, "Substrates for Use with Peroxidase-labeled Antibodies", pp. 29–31 (1990), describes immunoblotting with tetramethylbenzidine (TMB).
Kirkegaard & Perry Labs, Product Catalog, pp. 5–6 (Summer 1990) provides information concerning peroxidase substrates for immunoassays on membranes.
McKimm-Breschkin, J. Immunological Methods 135: 277–280 (1990), describes the use of TMB for solid phase immunoassays.
Modern Photographic Processing, vol. 2, pp. 453–553 (1979), describes the nature of color development and use of color developing agents such as p-phenylenediamines.

*Primary Examiner*—Michael G. Wityshyn
*Assistant Examiner*—Abdel A. Mohamed

[57] ABSTRACT

A substrate for detecting peroxidase activity in a peroxidase-based assay which includes a substantially aqueous solution of at least a 1-naphthol derivative and tetramethylbenzidine is described.

8 Claims, No Drawings

CHROMOGENIC SUBSTRATES FOR IMPROVING DETECTION IN A PEROXIDASE-BASED ASSAY

FIELD OF THE INVENTION

This invention relates to chromogenic substrates for determining peroxidase activity in an assay and, in particular, to substrates for improving detection in a peroxidase-based assay which utilize, inter alia, a substantially aqueous solution of tetramethylbenzidine and a naphthol derivative.

BACKGROUND OF THE INVENTION

Horseradish peroxidase ("HRP") is a commonly used enzyme label for immunological detection systems. HRP decomposes two molecules of hydrogen peroxide, the natural substrate, into water and oxygen. HRP initiates this reaction when it donates a pair of electrons to hydrogen peroxide. The enzyme subsequently extracts electrons (oxidizes) from a suitable donor. Some electron donors become activated upon the loss of electrons and may react with each other to form a polymer which precipitates. A donor that forms an intensely colored precipitate upon release of electrons (oxidation) makes a good HRP substrate for an immunological detection system.

The low specificity of HRP for the electron donor has allowed the development of many chromogenic substrates for HRP such as 4-chloro-1-naphthol ("4CN"), 3-amino-9-ethyl-carbazole ("AEC"), and 3,3'-diaminobenzidine ("DAB") and its derivatives. However, such substrates suffer from a number of disadvantages. For example, DAB is carcinogenic and 4CN is insensitive.

Conyers et al., Anal. Biochem., 192:207-211 (1991), describes two chromogenic systems for HRP detection on membranes which use the principle of the Nadi reaction. These systems use dimethyl or diethyl analogues of p-phenylenediamine with 4-chloro-1-naphthol to generate a blue product or 3-methyl-2-benzothiazolinone hydrazone with 4-chloro-1-naphthol to generate a red product. Bos et al., J. of Immunoassay, 2(3&4):187-204 (1981), describes the use of 3,3', 5,5'-tetramethylbenzidine ("TMB") as a non-mutagenic chromogen for HRP in enzyme-immunoassays. Brand et al., BioTechniques, 8(1): 58-60 (1990), describes a comparison of the performance and stability of two precipitating substrate systems for immunoblotting, namely, TMB and DAB. De Jong et al., Histochemical Journal 17:1119-1130 (1985), describes various visualization methods for peroxidase and alkaline phosphatase activity with respect to sensitivity, stability of chromogen solutions and final precipitates, background staining, and localization properties.

U.S. Pat. No. 4,596,770, issued to Parham et al. on Jun. 24, 1986, describes the use of aqueous N-methyl pyrrolidone as a solvent for a substrate containing tetraalkyl benzidine chromogen and a peroxide in determining peroxidase enzyme activity.

U.S. Pat. No. 4,503,143, issued to Gerber et al. on Mar. 5, 1985, describes the use of TMB or its derivatives as chromogenic substances for detection of antigen or antibody in colorimetric enzyme immunoassays.

U.S. Pat. No. 4,886,760, issued to Ben-Michael on Dec. 12, 1989, describes stable chemical compositions containing chromogenic materials and peroxides which can be used in chromogenic reactions.

Ben-Michael U.S. Pat. No. 4,849,342, issued to Ben-Michael on Jul. 18, 1989, describes a method for carrying out peroxidatively active enzyme assays when the enzyme is in free solution or in cell-bound form.

Nachlas et al., J. Histochem. Cytochem., 6:445-456(1958), describes 4-amino-1-N,N-dimethyl-naphthylamine useful as a reagent for the Nadi reaction which can provide a histochemical method for either cytochrome oxidase (G-Nadi) or peroxidase (M-Nadi).

European Patent Application Publication No. 271,713 published on Jun. 22, 1988 describes a method by means of which aqueous solutions containing chromogenic materials can be prepared from substantially anhydrous compositions containing all elements of the desired chromogen.

SUMMARY OF THE INVENTION

This invention relates to a substrate for improving detection in a peroxidase-based assay which comprises a substantially aqueous solution of at least a naphthol derivative and tetramethylbenzidine.

In another aspect this invention relates to a method for improving detection in a peroxidase-based assay which comprises reacting peroxidase with a substantially aqueous solution of at least a naphthol derivative and tetramethylbenzidine.

In still another embodiment this invention is directed to a peroxidase-based assay for detecting the presence or absence of a substance in a sample suspected to contain the substance wherein the improvement comprises improving detection of the substance by reacting peroxidase with a substantially aqueous solution of at least a naphthol derivative and tetramethylbenzidine.

DETAILED DESCRIPTION OF THE INVENTION

The term "peroxidase-based assay" means a solid phase enzyme assay in which a peroxidase enzyme, such as HRP, is used as the enzyme label.

The term "substantially aqueous solution" means a solution containing primarily water and, perhaps, small amounts of other components such as a water-miscible solvent, buffer salts, etc.

The term "tetramethylbenzidine" ("TMB") means 3,3', 5,5'-tetramethylbenzidine and derivatives thereof, e.g., water soluble salts of TMB.

The term "naphthol derivative" means unsubstituted and substituted naphthols.

The term "phenylenediamine derivative" means unsubstituted and substituted phenylenediamines whether in salt or free base form. Those skilled in the art will appreciate that phenylenediamines are organic bases which are unstable in air. They are usually reacted with inorganic acids, such as hydrochloric or sulfuric, or with organic acids such as p-toluenesulfonic acid, to form salts that are easier to purify and are more stable during storage. However, it is the free base which is the active developing form.

The chromogenic substrate of the invention comprises a substantially aqueous solution of at least a naphthol derivative and tetramethylbenzidine or a naphthol derivative, tetramethylbenzidine, and a phenylenediamine derivative. Either combination overcomes the toxicity problems associated with using DAB, the sensitivity problems encountered using a chromogen such as 4CN alone, and the problems associated with using a chromogen such as TMB alone, for example, stability of the precipitate, background, and a tendency of the precipitate to "wash off."

Thus, the substrate of the invention overcomes the above-mentioned problems by producing: (i) sensitivity greater than that produced by using the chromogen alone, (ii) very low background, (iii) a stable precipitate, and (iv) a final color similar to that produced as if the chromogen were used alone, i.e., in the absence of TMB.

The amount of chromogen present in the substrate solution can vary over a considerable range depending upon the identity and concentration of the peroxidase enzyme whose activity is to be measured. When the chromogen comprises a combination of a naphthol derivative, such as 4CN, and TMB, the concentration of the naphthol derivative can range from $10^{-4}$ M to $10^{-2}$ M and the concentration of TMB can range from $10^{-4}$ M to $10^{-3}$ M. Preferably, the naphthol derivative is present in an amount from $1 \times 10^{-3}$ M to $2 \times 10^{-3}$ M and TMB is present in an amount from $5 \times 10^{-4}$ M to $7.5 \times 10^{-4}$ M.

When the chromogen comprises a tripartite combination of a naphthol derivative, such as 4CN, TMB, and a phenylenediamine derivative the concentration of a naphthol derivative can range from $10^{-4}$ M to $10^{-2}$ M and preferably from $1 \times 10^{-3}$ M to $2 \times 10^{-3}$ M, the concentration of TMB can range from $10^{-4}$ M to $10^{-3}$ M and, preferably, from $1 \times 10^{-3}$ M to $2 \times 10^{-3}$ M, and the concentration of the phenylenediamine derivative can range from $10^{-4}$ M to $10^{-3}$ M and, preferably, from $1.5 \times 10^{-4}$ M to $4 \times 10^{-4}$ M.

The amount of peroxide present can also vary depending upon the amount and type of chromogen present. The concentration can range from 0.001% to 0.03% and preferably from 0.003% to 0.01%. Any of the usual peroxides such as hydrogen peroxide, urea peroxide, or the like can be employed in the substrate solution. It is also desirable to include a buffer in the solution such as acetate which maintains the pH in the range from 4 to 7. The preferred buffer is citrate/acetate as described below which maintains the pH around 5.

Any unsubstituted or substituted naphthol derivatives can be used to practice the invention. There can be mentioned 4CN, 1-naphthol, 2-naphthol, 1,5-naphthylene diol, 1,6-naphthylene diol, 2,7-naphthylene diol, 6-amino-1-naphthol, 5-amino-1-naphthol, and the like.

The substrate solution of the invention is preferably freshly prepared before use by mixing 50 μl to 200 μl of a first stock solution of a naphthol derivative such as 4CN made at 19.65 mg/ml in dimethylsulfoxide (DMSO) and 40 μl to 300 μl of a second stock solution of TMB made at 6 mg/ml in DMSO in approximately ten ml of the citrate/acetate buffer as described below.

In another embodiment the substrate solution of the invention can be made as described below in Example 2 wherein a naphthol derivative, a phenylenediamine derivative, and TMB are used.

Examples of phenylenediamine derivatives which can be used to practice the invention include N,N-diethyl-p-phenylenediamine monohydrochloride, N,N-diethyl-p-phenylenediamine sulfur dioxide complex, N,N-diethyl-p-phenylenediamine sulfate, N,N-diethyl-3-methyl-p-phenylenediamine hydrochloride or 2-amino-5-diethylaminotoluene hydrochloride, N-ethyl-N-(β-hydroxyethyl)-p-phenylenediamine sulfate, N-ethyl-N-(β-hydroxyethyl)-3-methyl-p-phenylenediamine sulfate, N-ethyl-N-(β-methylsulfonamidoethyl)-3-methyl-p-phenylenediamine sesquisulfate monohydrate, 4-amino-N-ethyl-N-(2-methoxyethyl)m-toluidine di-toluene-sulfonate, bis-CD4, and the like.

The substrate solution of the invention can be used with most solid phase assay systems in which a peroxidase is used as the enzyme label such as for histochemical staining, nucleic acid assays, immunoassays, etc. The preferred solid phase system for an enzyme immunoassay is a membrane. For histochemical staining, the solid phase is the medium itself, e.g., animal or plant tissue, generally affixed to a glass or plastic slide.

The improvement of the present invention can be used to detect the activity of any enzyme which catalyzes the reaction of the chromogen with peroxide to form a colored compound, such as, horseradish peroxidase.

The determination of peroxidase activity is carried out in the usual manner by incubating the substrate solution with the sample containing the enzyme to develop a visible color.

In another embodiment, this invention concerns a method for improving detection in a peroxidase-based assay which comprises reacting peroxidase with a substantially aqueous solution of at least a naphthol derivative and tetramethylbenzidine. This method is illustrated in the examples below.

In still another embodiment this invention is directed to a peroxidase-based assay for detecting the presence or absence of a substance in a sample suspected to contain the substance wherein the improvement comprises improving detection of the substance by reacting peroxidase with a substantially aqueous solution of at least a naphthol derivative and tetramethylbenzidine.

Such assays can be performed using conventional technology well known to those skilled in the art. Any type of antigen can be detected using the present invention.

The following examples are intended simply to illustrate the invention and are not intended in any way to limit the invention.

EXAMPLE 1

Nitrocellulose membranes (Grade BA83, Schleicher & Schuell, Keene, NH) were cut into 1cm×8 cm strips and spotted with 1 microliter of rabbit IgG diluted serially two-fold starting at 250 ng/ml. The membranes were blocked with 5% non-fat dry milk in phosphate buffered saline -0.05% Tween 20 (PBST) for one hour at room temperature. The membranes were then incubated with 10 ml of an anti-rabbit IgG-HRP conjugate for one hour at room temperature and washed with PBST.

The resulting IgG-anti-IgG-HRP complex was detected using a number of chromogenic compositions to compare the result obtained using a TMB-4CN system versus DAB, 4CN alone and TMB alone.

The chromogenic compositions were prepared as follows:

(1) DAB (Sigma, St. Louis, Mo.) was used at a concentration of 0.5 mg/ml in 50 mM Tris-HCL, 0.1 M imidazole, 0.01% $H_2O_2$.

(2) A stock solution of 4CN (Sigma) was made at 19.65 mg/ml in dimethylsulfoxide (DMSO).

(3) A stock solution of TMB (Aldrich, Milwaukee, Wis.) was made at 6 mg/ml in DMSO.

(4) A stock solution of TMB dihydrochloride (Sigma) was made at 7.83 mg/ml in methanol.

An 0.1 M citrate/0.1 M acetate buffer, pH 5.0 containing 0.003% $H_2O_2$ was used to prepare the TMB/4CN chromogenic system. The volumes of TMB and 4CN used are set forth in Table 1 below.

Chromogens were added to the membranes for ten minutes at room temperature, washed with water, and dried before evaluating the results. Table 1 lists the volumes of each stock solution added to ten ml of citrate/acetate buffer and the number of spots visualized.

TABLE 1

| Strip | Volumes | Spots |
|---|---|---|
| 1 | DAB Control | 5 |
| 2 | 200 μl TMB dihydrochloride, 100 μl 4CN | 5 |
| 3 | 100 μl 4CN | 2 |
| 4 | 300 μl TMB | 0 |
| 5 | 300 μl TMB, 100 μl 4CN | 5 |

The TMB/4CN (TMB as free base or salt) chromogenic system used in strips 2 and 5 provided a color similar in hue to that produced using 4CN alone and substantially greater in intensity than using 4CN or TMB alone, resulting in the ability to distinguish extra spots.

EXAMPLE 2

Nitrocellulose membranes (Grade BA83 from Schleicher & Schuell, Keene, NH) were spotted with 1 microliter of HRP diluted serially three fold starting at 28 micrograms/ml.

Chromogens were made as follows:

(1) A stock solution was made of 0.075M TMB in DMSO:dimethylformamide (3:1).

(2) A stock solution was made of 0.11M 4CN in methanol.

(3) A stock solution was made of 0.075M bis-CD4 in DMSO;dimethylformamide (3:1). Bis-CD4 was made as described in L. Plambeck et al., J. Imaging Science 30:224–227 (1986).

Chromogens were added to the membranes for ten minutes at room temperature, washed with water, and dried before evaluating the results. Table 2 lists the volumes of each stock solution added to ten ml of 0.1 M citrate, 0.1 M acetate buffer, pH 5.0 containing 0.003% $H_2O_2$, and the number of spots visualized.

TABLE 2

| Strip | Volumes | Spots |
|---|---|---|
| 1 | 100 μl TMB, 100 μl 4CN | 4 |
| 2 | 100 μl bis-CD4, 100 μl 4CN | 2 |
| 3 | 50 μl bis-CD4, 100 μl 4CN, 50 μl TMB | 4 |
| 4 | 20 μl bis-CD4, 100 μl 4CN, 100 μl TMB | 4 |

The addition of TMB to the bis-CD4/4CN chromogenic system greatly enhanced sensitivity when compared to using bis-DC4/4CN alone. The color of the spots in strip 1 was similar to that obtained when using 4CN alone (bluish-grey). The color of the spots in strips 2 through 4 was dark blue.

What is claimed is:

1. A substrate for detecting peroxidase activity in a peroxidase-based assay which comprises a substantially aqueous solution of at least a 1-naphthol derivative and tetramethylbenzidine.

2. A substrate according to claim 1 in which the 1-naphthol derivative is 4-chloro-1-naphthol.

3. A substrate according to claim 1 in which the substantially aqueous solution further comprises a phenylendiamine derivative.

4. A substrate according to claim 2 in which the substantially aqueous solution further comprises a phenylenediamine derivative.

5. In peroxidase-based assay for detecting the presence or absence of a substance in a sample suspected to contain the substance wherein the improvement comprises improving detection of the substance by reacting peroxidase with a substantially aqueous solution of at least a 1-naphthol derivative and tetramethylbenzidine.

6. An assay according to claim 6 wherein the 1-naphthol derivative is 4-chloro-1-naphthol.

7. An assay according to claim 5 wherein the substantially aqueous solution further comprises a phenylendiamine derivative.

8. An assay according to claim 6 wherein the substantially aqueous solution further comprises a phenylendiamine derivative.

* * * * *